US006292527B1

(12) United States Patent
Guendel

(10) Patent No.: US 6,292,527 B1
(45) Date of Patent: Sep. 18, 2001

(54) METHOD FOR OPERATING A COMPUTED TOMOGRAPHY (CT) DEVICE

(75) Inventor: Lutz Guendel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/586,291

(22) Filed: Jun. 2, 2000

(30) Foreign Application Priority Data

Jun. 2, 1999 (DE) .................................................. 19925395

(51) Int. Cl.$^7$ ........................................................ A61B 6/03
(52) U.S. Cl. ................................................. 378/15; 378/4
(58) Field of Search ................... 378/15, 4, 21, 378/19

(56) References Cited

U.S. PATENT DOCUMENTS

| | | |
|---|---|---|
| 5,247,556 | 9/1993 | Eckert ........................................ 378/4 |
| 5,262,946 * | 11/1993 | Heuscher ........................ 364/413.18 |
| 5,412,702 | 5/1995 | Sata ........................................... 378/4 |
| 5,796,803 | 8/1998 | Flohr et al. ............................. 378/15 |
| 5,999,587 * | 12/1999 | Ning et al. ................................ 378/4 |
| 6,188,745 * | 2/2001 | Gordon .................................... 378/19 |

FOREIGN PATENT DOCUMENTS

| | | | |
|---|---|---|---|
| 198 00 946 | 7/1999 | (DE) . | |
| 0-531 993-A1 * | 3/1993 | (EP) ................................ A61B/6/03 |

* cited by examiner

Primary Examiner—Robert H. Kim
Assistant Examiner—Irakli Kiknadze
(74) Attorney, Agent, or Firm—Schiff Hardin & Waite

(57) ABSTRACT

In a method for operating a computed tomography (CT) device, having a detector system formed by an array of detector elements that are arranged in rows that extend substantially in the direction of the system axis and also are arranged in columns, the generation of an X-ray shadow image ensues by implementation of a volume scanning, extraction of the data belonging to a desired projection direction from data supplied by a number of rows of the detector system given the volume scanning, and reconstruction of the X-ray shadow image on the basis of the extracted data.

8 Claims, 4 Drawing Sheets ent invention is to provide a method
METHOD FOR OPERATING A COMPUTED TOMOGRAPHY (CT) DEVICE

BACKGROUND OF THE INVENTION

1. Field of the Invention

The present invention relates to a method for operating a computed tomography (CT) device, of the type having an X-ray source at least the focus of which is, i.e. plane or curved at least two-dimensional displaceable around a system axis, a detector system, formed by a planar/array of detector elements that are arranged in rows that extend substantially transverse to the direction of the system axis and that also are arranged in columns, wherein the detector system picks up X-rays emitted from the X-ray source, and a support device for an examination subject, wherein the focus of the X-ray source is displaced around the system axis for scanning a volume of the examination subject for generating an X-ray shadow image of the examination subject is obtained.

2. Description of the Prior Art

The following method for operating the CT device is normally utilized for carrying out an examination by means of a CT device. An X-ray shadow image (topogram) is generated when the X-ray source does not rotate, with the examination subject being moved on the support device relative to the X-ray source and the detector system is moved in the direction of the system axis. The area of the examination subject to be acquired is defined, in the actual examination, in the direction of the system axis on the basis of the generated X-ray shadow image. The examination subject is positioned by moving the support device to the start point of the examination subject's defined area to be acquired. The actual examination is then conducted, usually in the form of a spiral scan.

This method is associated with a few basic disadvantages. The entire procedure is relatively long, which is undesired for reasons of efficiency and also for medical reasons, particularly with respect to emergency patients. Also, when X-ray shadow images from different projection directions (angles of view) are desired, for example "from front" and "from the side", the patient is moved three times with the patient bed—namely twice for purposes of generating the shadow images and a third time for the spiral scan. There is the danger of the examination results being falsified due to movements of the patient between X-ray shadow images and spiral scan. The generation of one or more X-ray shadow images means an additional radiation exposure for the patient to be examined.

In a CT apparatus having a detector system with only one row of detector elements, these disadvantages can be theoretically avoided by the method known from European Application 0 531 993 and German OS 41 03 588, since merely a spiral scan is carried out and the data that are required for the reconstruction of the X-ray shadow image, from one or more projection directions, are extracted from the thereby-acquired data and are correspondingly processed. The resulting X-ray shadow image, or the resulting X-ray shadow images, keeping pace with tomograms that are reconstructed in parallel with the X-ray shadow image-reconstruction, are shown together on a display unit. However, in practical operation the image quality of the X-ray shadow image is insufficient, particularly when disadvantageous operating parameters are utilized, such as a slice thickness greater than 2 mm and/or a relation of bed advance per rotation to slice thickness (pitch) of greater than 1.

SUMMARY OF THE INVENTION

An object of the present invention is to provide a method of the aforementioned type wherein the conditions are present to enable X-ray shadow images of high quality to be generated on the basis of a spiral scan that is carried out with disadvantageous operating parameters.

According to the invention, this object is achieved in a method for operating a computed tomography (CT) device, having an X-ray source at least the focus of which is displaceable around a system axis, a detector system, formed by a planar array of detector elements that are arranged in rows that extend substantially transverse to the direction of the system axis and that also are arranged in columns, wherein the detector system picks up the X-rays emitted by the X-ray source and a support device for an examination subject, wherein at least the focus of the X-ray source is displaced around the system axis for scanning a volume of the examination subject and wherein the generation of an X-ray shadow image of the examination subject ensues by means of the steps of implementing a volume scanning, extracting data that belongs to a desired projection direction from data supplied by a number of rows of the detector system in the volume scanning, and reconstructing the X-ray shadow image on the basis of the extracted data.

In a preferred embodiment of the invention, the volume scanning can be carried out in the form of a spiral scan; for this purpose, the support device, and the X-ray source and the detector system, are relatively displaced substantially in the direction of the system axis while rotating the X-ray source (or at least its focus) around the system axis.

Alternatively, the support device, and the detector system, and the X-ray source can assume a fixed position relative to one another in the direction of the system axis when the volume is scanned. In this case, the extent of the area of the examination subject covered by the volume scan in the direction of the system axis is determined by the size of the array of detector elements in the direction of the system axis, or is determined by the extent of the area of the array utilized for the volume scan in the direction of the system axis, if the entire array is not been utilized.

Regardless of the type of volume scan, the inventive method is based on the utilization of a CT device with a detector system, which does not have a single row of detector elements, but has a planar array with a number of rows of detector elements, and, from the data acquired in the course of the volume scan, preferably in the form of a spiral scan, the inventive method not only utilizes the data from one row of the detector system but utilizes data supplied by a number of rows of the detector system in order to reconstruct the X-ray shadow image.

As long as the collimated slice thicknesses do not substantially exceed 2 mm regarding the data supplied by the rows of the detector system, on which data the reconstruction of the X-ray shadow image is based, and as long as it is guaranteed—in the case of a volume scan in the form of a spiral scan—that the advance per rotation of the X-ray source focus does not exceed the total width of the detector rows supplying the data on which the reconstruction of the X-ray shadow image is based, the conditions for a high image quality of the X-ray shadow image exist.

In a version of the invention, at least one tomogram is reconstructed on the basis of the data acquired during the volume scan and the extraction of the data for the X-ray shadow image ensues prior to the reconstruction of the tomogram. It is thereby guaranteed that the processing of the data acquired during the volume scanning does not influence the image quality of the X-ray shadow image. The processing ensues in the course of the reconstruction of the tomogram. This is particularly important when, in an embodiment of the invention, the data of a number of rows of the detector system are combined for reconstructing the tomogram, for example, in order to be able to reconstruct tomograms of slices, whose thickness is larger than the width of a detector row. In this case, the combination of the data of a number of rows of the detector system does not affect the image quality of the X-ray shadow image.

Therefore, keeping pace—i.e. parallel to the volume scanning—X-ray shadow images of high quality and tomograms can be reconstructed and displayed by means of the inventive method.

If the data are picked up in fan geometry in a version of the invention the data are converted into parallel geometry for avoiding specific image artefacts in the X-ray shadow image that are caused by the fan geometry.

To improve the resolution in the direction of the system axis, in accordance with the invention data are extracted regarding the desired projection direction and regarding a projection direction that is offset to it by 180° and the data are used for reconstructing the X-ray shadow image of the desired projection direction, and when the data are acquired in fan geometry, it is advantageous to utilize data that are converted to parallel geometry (in the described way) regarding the desired projection direction and regarding the projection direction that is offset thereto by 180°; such data therefore are not extracted in parallel geometry before the data of the spiral scan have been converted.

When the CT device has a detector system with rows of detector elements of different width, and when data of rows with detector elements of different width are extracted, in an exemplary embodiment of the invention the extracted data, prior to the reconstruction of the X-ray shadow image, are converted to data as are acquired by a detector system with equidistant rows of detector elements of equal width.

DESCRIPTION OF THE PREFERRED EMBODIMENTS

Figure 1:
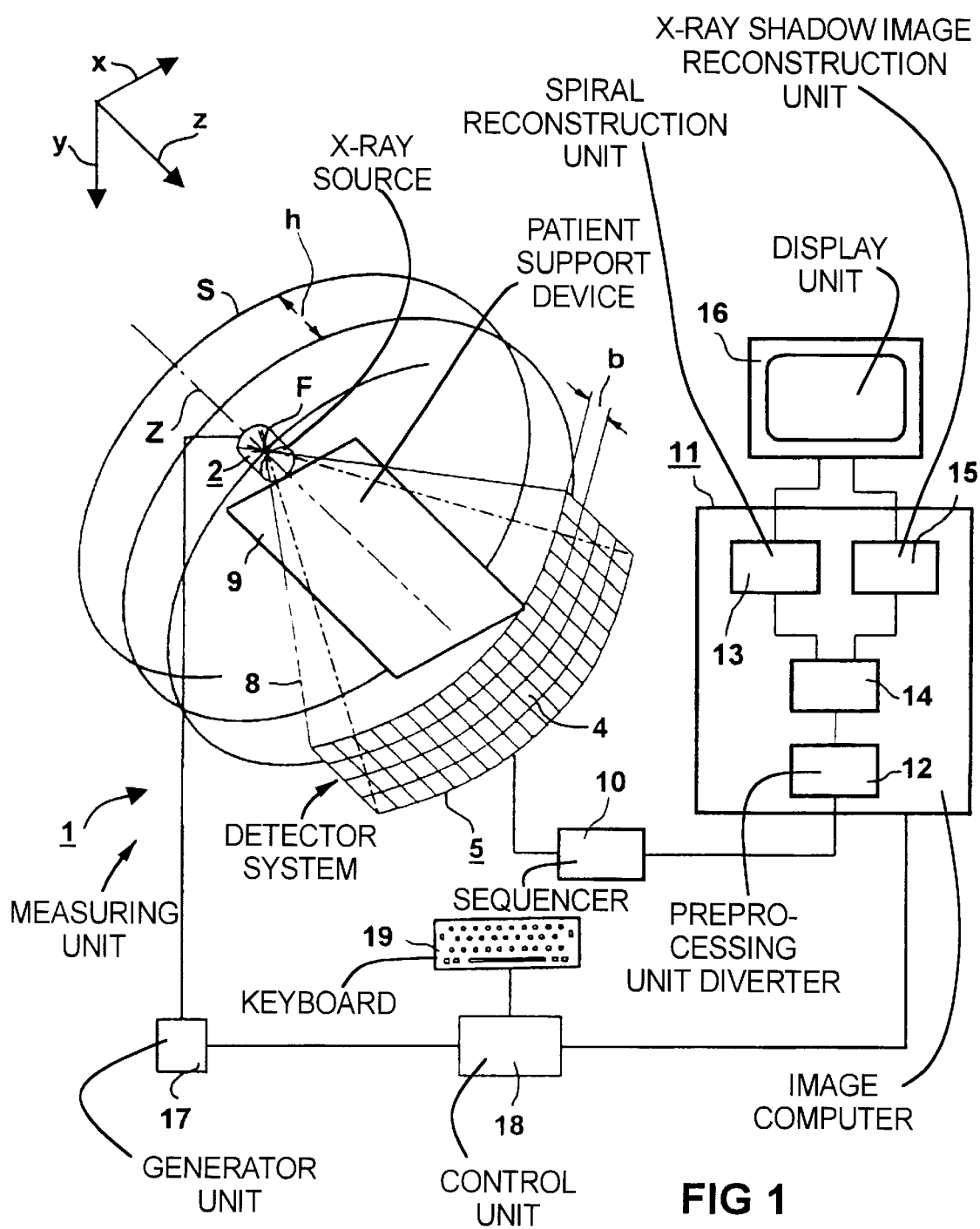
FIG. 1 is a perspective view and a block diagram illustration of a CT device suitable for implementing the inventive method.
Figure 2:
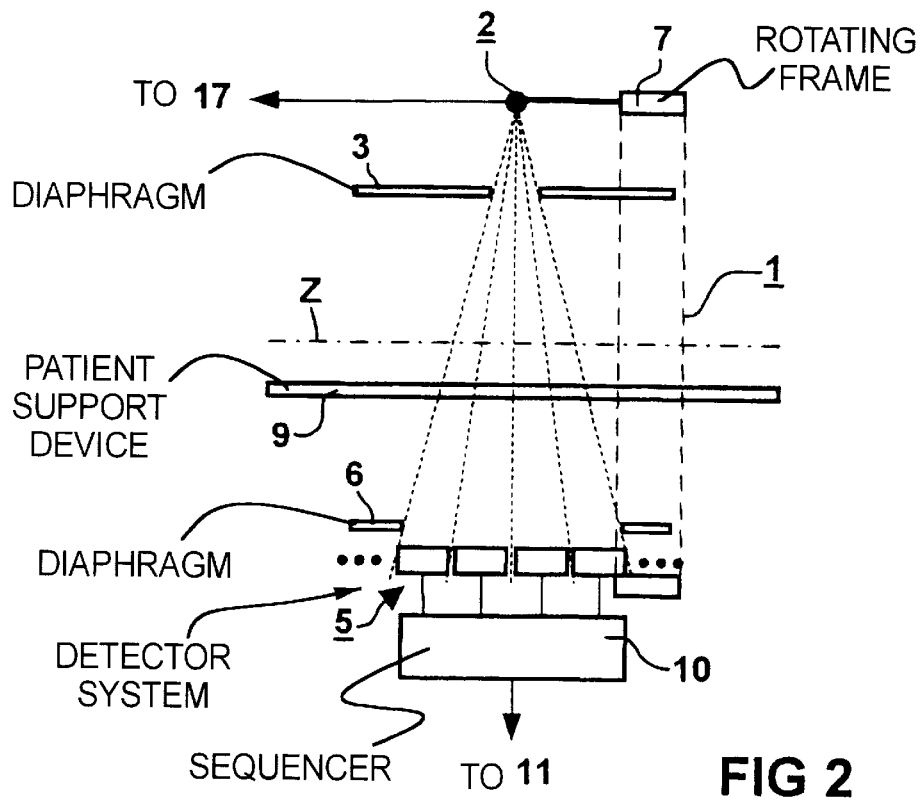
FIG. 2 shows a longitudinal section through the device according to FIG. 1.

FIGS. 1 and 2 show a CT device of the $3^{rd}$ generation that is suitable for implementation of the inventive method. Its measuring unit (which is referenced 1) includes an X-ray source 2 with a radiation diaphragm 3 in front of the X-ray source and which is close to the source 2 (FIG. 2). The measuring arrangement 1 also has a detector system 5 that is fashioned as a planar array of a number of rows and columns of detector elements, one of which is referenced 4 in FIG. 1. The detector system 5 is preceded by a diaphragm 6 that is close to the detector (FIG. 2). The X-ray source 2 with the diaphragm 3, and the detector system 5 with the diaphragm 6 are attached to a rotating frame 7 (gantry) so as to be opposite to one another (as can be seen from FIG. 2) such that, during the operation of the CT device, a pyramid-shaped X-ray bundle with marginal rays 8, and which is emitted from the X-ray source 2 and which is faded in by the adjustable diaphragm 3, is incident on the detector system 5. The diaphragm 6 is adjusted corresponding to the cross section of the X-ray bundle that has been adjusted by the diaphragm 3 such that only the area of the detector system 5 is exposed, which can be directly struck by the X-ray bundle. These are four rows of detector elements according to the operating status shown in FIGS. 1 and 2. FIG. 2 indicates (by dotted lines) that further rows of detector elements, which are covered by the ray diaphragm 6, are present.

The rotating frame 7 can be rotated by a drive means (not shown) around a system axis Z. The system axis Z extends parallel to the z-axis of a Cartesian coordinate system (shown in FIG. 1).

The columns of the detector system 5 also extend in the direction of the z-axis, whereas the rows, whose width b is measured in the direction of the x-axis and which, for example, is 1 mm, extend transverse to the system axis Z and thus transverse to the z-axis.

For example, in order to be able to place a patient into the beam path of the X-ray bundle, a support device 9 is provided that can be displaced parallel to the system axis Z, in the direction of the z-axis, with a synchronization between the rotational motion of the rotating frame 7 and the translational motion of the support device 9 being such that the relation of translational rate and rotational rate is constant. This relation is adjustable in that a desired value is selected for the advance h of the support device 9 per rotation of the rotating frame 7.

Therefore, a volume of an examination subject situated on the support device 9 can be examined in the course of a volume scanning, the volume scanning being undertaken in the form of a spiral scan with a number of projections being picked up from different projection directions, per revolution of the measuring unit 1 with simultaneous rotation of the measuring unit 1 and translation of the support device 9. In this spiral scan, at least the focus F of the X-ray source moves relative to the support device 9 on a spiral path S shown in FIG. 1.

The measurement data that are read out from the detector elements of each row of the detector system 5 during the spiral scan and that correspond to the individual projections are serialized in a sequencer 10 and are transferred to an image computer 11.

After the measurement data have been pre-processed in a processing unit 12 of the image computer 11, the resulting data stream reaches a tomogram reconstruction unit 13, which, according to a known method (e.g. 18OLI- or 36OLI- interpolation), reconstructs tomograms of desired slices from the measurement data.

In order to be able to determine, in the z-direction, the position of a slice for which a tomogram is to be reconstructed, an X-ray shadow image, apart from tomograms, can also be reconstructed from the measurement data. For this purpose, the portion of the measurement data required for reconstructing an X-ray shadow image of a desired projection direction is extracted from the data stream coming from the sequencer 10, before it reaches the tomogram reconstruction unit 13, by means of a diverter 14, and this portion is supplied to an X-ray shadow image reconstruction unit 15, which, according to a known method, reconstructs an X-ray shadow image from the extracted measurement data.

The tomograms or X-ray shadow images respectively reconstructed by the tomogram image reconstruction unit 13 and the X-ray shadow image reconstruction unit 15 during the spiral scan are displayed at a display unit 16, e.g at a video monitor, which is connected to the image computer 11, parallel to and synchronously with the spiral scan.

A generator unit 17 provides the X-ray source 2—for example an X-ray tube—with the necessary voltages and currents. In order to be able to adjust these according to the respectively necessary values, a control unit 18 with a keyboard 19 is allocated to the generator unit 17, which control unit allows the necessary adjustments.

The other operation and control of the CT device also ensues by means of the control unit 18 and the keyboard 19; this is shown in that the control unit 18 is connected to the image computer 11.

The structure of the image computer 1 has been described as if the preprocessing unit 12, the tomogram image reconstruction unit 13, the diverter 14 and the X-ray shadow image reconstruction unit 15 were hardware components. These components, however, are normally realized by means of software modules, which run on an all-purpose computer that is provided with the required interfaces and that, different from FIG. 1, can also assume the function of the control unit 18.

Figure 3:
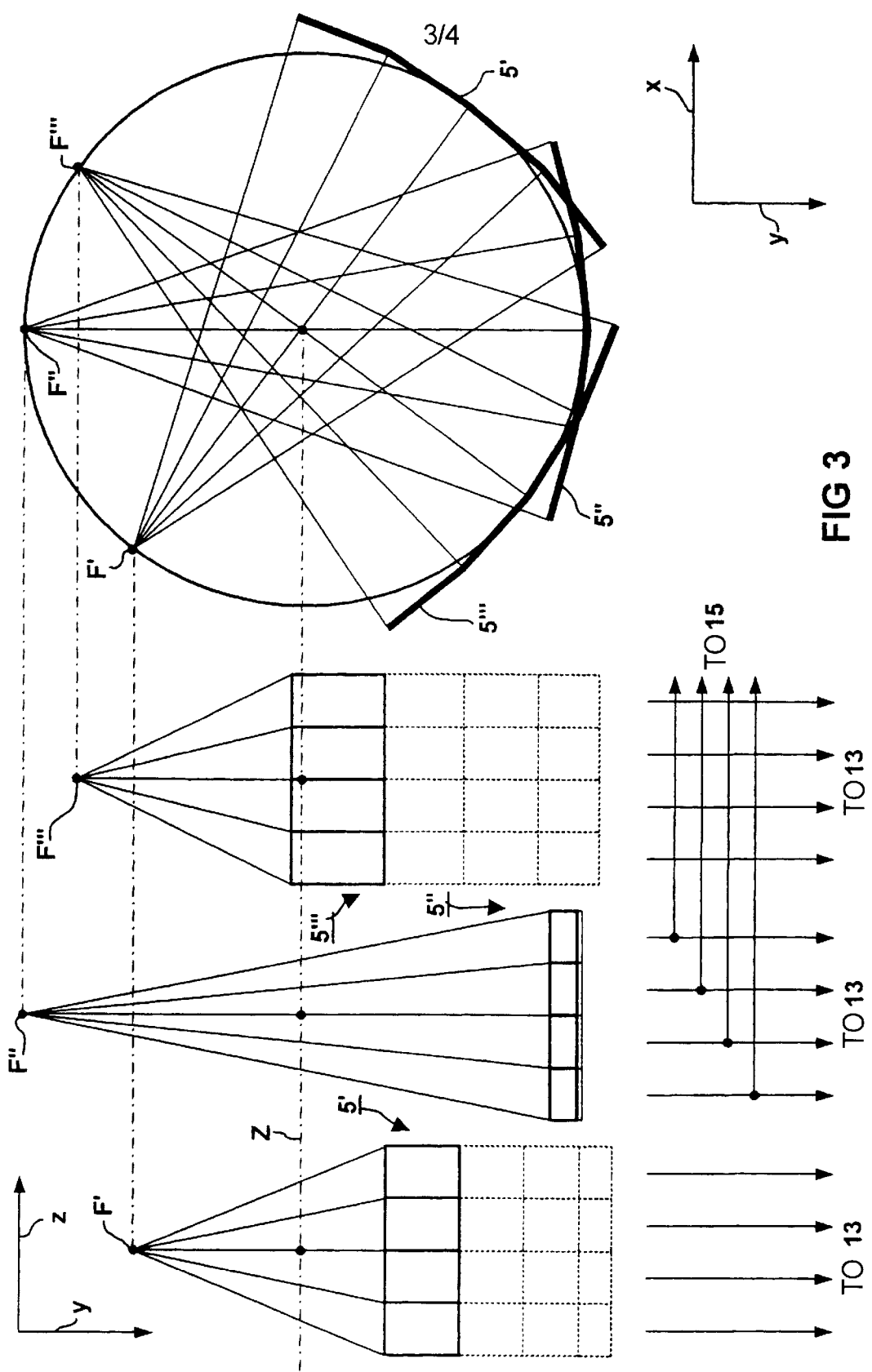
FIGS. 3–4 are diagrams illustrating the inventive method.
Figure 4:
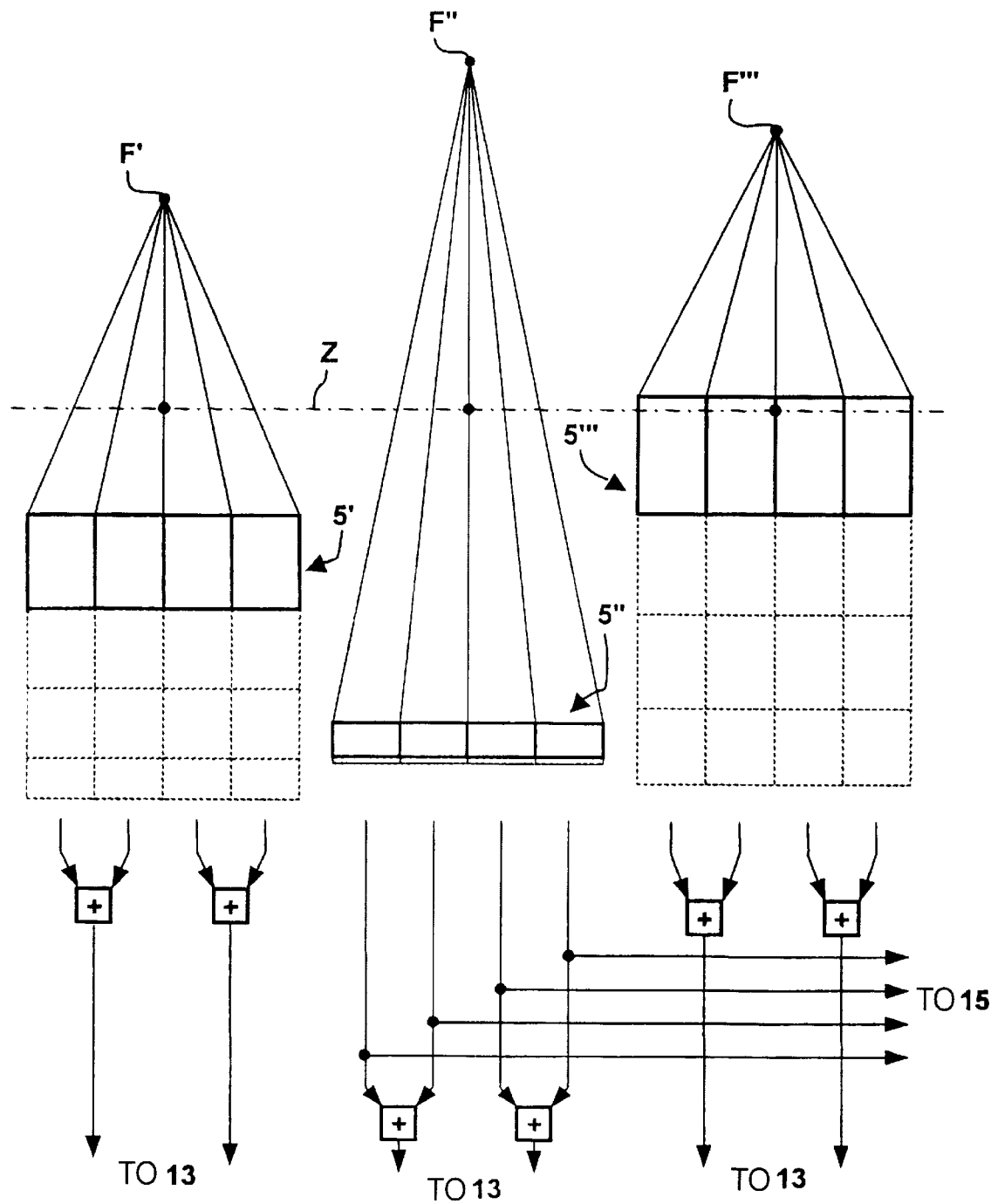

FIGS. 3 and 4 show how the measuring data are extracted, which are required for reconstructing an X-ray shadow image for a specific projection direction.

For three exemplary projections, FIG. 3 shows the positions of the X-ray source F', F" and F"', as well as the appertaining positions of the detector system 5', 5" and 5"', one in the xy-plane (right side) and one in the yz-plane (left side) in case of four rows of the detector system 5 being active (as shown in FIG. 2), with only four detector elements per row being considered in FIG. 3. Four detectors per detector row can be seen in the yz-plane in the positions F' and F"'; two detector elements per detector row are covered in the position F", i.e. only two can be seen. For clarity, only the beam path of one detector element per detector row is shown by means of a continuous line. The other detector elements are shown by means of a dotted line. The yz-plane is shown by means of the arrows allocated to the detector system 5 in the respective positions 5', 5" and 5"'. Only the measurement data of the individual rows of the detector system 5 in these plane positions—which measurement data correspond to the respective projections—reach the tomogram reconstruction unit 13 or the tomogram image reconstruction unit and the X-ray shadow image reconstruction 15.

The point of origin of the coordinate system of FIG. 4 is situated on the moved support device 9. Therefore, different positions of the detector 5', 5" and 5"' can be recognized in the xz-plane and in the yz-plane for different tube positions F', F" and F"'.

As can be seen in FIG. 3, the measurement data for all picked up projections arrive at the tomogram reconstruction unit 13, whereas only the measurement data that correspond to the projection direction F"/5", which is the desired projection direction of the X-ray shadow image with the pickup direction "from front", are supplied to the X-ray shadow image reconstruction unit 15.

Therefore, X-ray shadow images of high image quality can be reconstructed, for example, given an expansion of the detector elements in the z-direction of 1 mm—independently of how the measurement data are further processed by the tomogram reconstruction unit 13—, as long as the advance of the support device 9 in the z-direction does not significantly exceed the total width of the four active rows of the detector system 5, namely 4 mm, per revolution of the measurement unit 1, since the examination subject can then be scanned in the z-direction essentially without interruptions.

The tomogram reconstruction unit 13 takes all measurement data into consideration when tomograms of slices of a thickness of 1 mm are to be reconstructed by means of the tomogram reconstruction unit 13.

The data from adjacent rows of the detector system 5 are appropriately combined in a known way for reconstructing tomograms when tomograms of slices of larger thickness—for example 2 mm—are to be reconstructed (as shown in FIG. 4 for the yz-plane, in a way analogous to FIG. 3). FIG. 4 shows this by means of squares that are provided with "+" signs, with the data of two rows of the detector system being supplied to the squares, which respectively provide only one dataset to the tomogram image reconstruction unit 13, which dataset corresponds to the combined measurement data of the two rows. However, the data for the reconstruction of the X-ray shadow image of the projection direction F"/5" are extracted and are supplied to the X-ray shadow image reconstruction unit 15, prior to the combination of the measurement data of adjacent rows of the detector system 5. As a result thereof, the combination of the measurement data does not influence the image quality of the X-ray shadow image.

For increased resolution in the z-direction, it is possible in the framework of the invention to also utilize measurement data, for the reconstruction of the X-ray shadow image, which were picked up in a projection direction that is offset by 180° relative to the desired projection direction of the X-ray shadow image. Therefore, not only the measurement data that correspond to the desired projection direction of the X-ray shadow image are extracted and supplied to the X-ray shadow image reconstruction unit 15, but also the measurement data of the projection direction that is offset thereto by 180°. Alternatively, the advance of the support device 9 in the z-direction, per revolution of the measuring unit 1, can be increased in this case beyond the total width of the four active rows of the detector system 5, namely beyond 4 mm in the case of the described exemplary embodiment, given the same resolution in the z-direction.

In the CT device according to FIGS. 1 and 2, the measurement data are acquired in fan geometry, i.e. that the measuring data, from a row of the detector system 5, are acquired by means of a fan-shaped X-ray bundle emitted from the focus of the X-ray source. Geometrical distortions occur in the case of the fan geometry, since the resolution is greater close to the X-ray source 2 than close to the detector system 5. These distortions can be avoided when the fan geometry is converted to parallel geometry, i.e. data are calculated for one projection direction from the data for a number of projection directions that are present in fan geometry, which data would correspond to the data that would be received for this projection direction if an X-ray bundle with parallel X-rays were incident on the detector elements. In the framework of the invention, this algorithm, which is known as "rebinning", can be utilized reconstructing tomograms and for purposes of reconstructing X-ray shadow images—either with or without use of the measurement data offset by 180° relative to the desired projection direction, and is executed by means of the preprocessing unit 12.

The generator unit 17 allows the following operating modes that can be adjusted by the control unit:
1. Continuous operation given spiral scanning with a radiographic performance that is parameterized for the generation of tomograms, 2. Continuous operation given spiral scanning with a radiographic performance that is parameterized for the generation of X-ray shadow images and that is reduced relative to the operating mode 1,
3. Switching mode, in which the X-ray source is situated in a position that corresponds to the projection direction that is desired for the X-ray shadow image, the X-ray source emits an X-ray pulse with operation that is parameterized for generating X-ray shadow images, and
4. Switch-off mode, in which the X-ray source is not activated.

Thus, the operating mode 3, for example, can be used at the beginning of the examination and only the X-ray shadow image is reconstructed and displayed.

Alternatively, at the beginning of the examination, the X-ray shadow image and the tomogram can be reconstructed in parallel in the operating mode 2. The results are displayed parallel at the display unit 16. The tomograms can only be tentatively utilized for diagnosis due to the reduced radiographic performance.

When diagnostically relevant structures are achieved in the operating mode 2 or 3, it is changed over to the operating mode 1, in which measurement data are acquired that make it possible, as a result of the higher radiographic performance, to reconstruct tomograms of high quality, which are displayed at the same time as the X-ray shadow image.

After the diagnostically relevant area has been scanned, the device is changed over to the operating mode 4 and the radiation is switched off.

In an alternative operating mode, which is especially important for CT devices whose detector system 5 is of a large width in the direction of the system axis Z and therefore has a large number of rows, a relative movement between the measuring unit 1 and the support device 9 in the direction of the system axis Z and therefore a spiral scan can be foregone when the extent of the detector system 5 is sufficient in order to cover the entire area to be examined. If the extent of the detector system S in the direction of the system axis Z is larger than the corresponding extent of the area to be examined, it is sufficient to activate only the rows of the detector system 5 that are necessary to cover the area to be examined.

Figure 5:
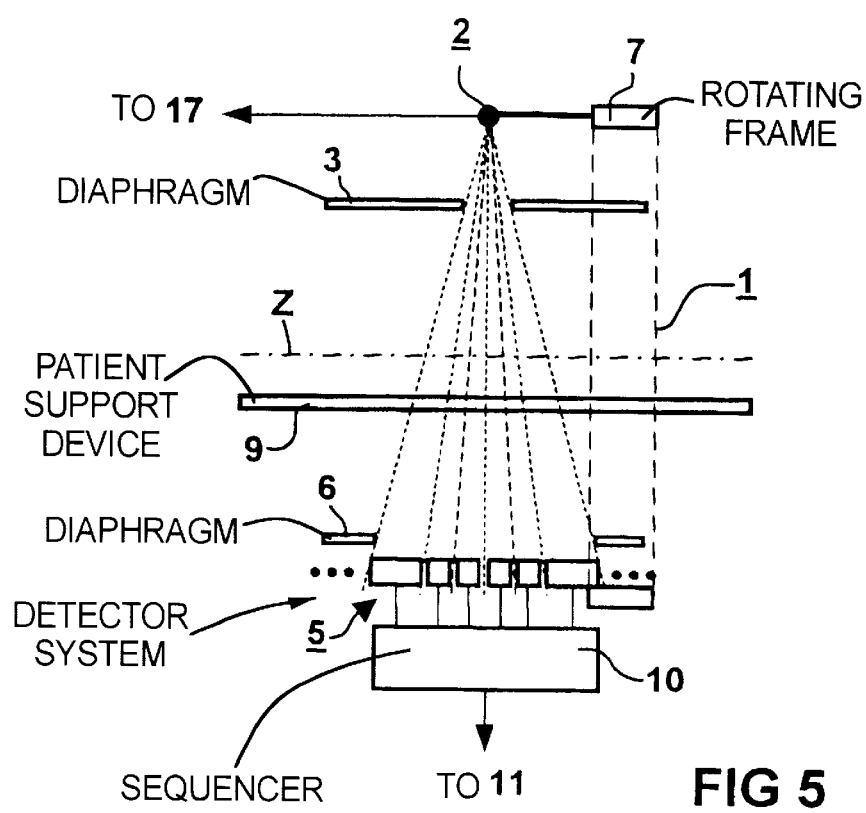
FIG. 5, analogously to FIG. 2, illustrates a further version of the invention.

The CT device according to FIG. 5 differs from the previously described one in that the detector system 5 has rows, whose width, which is measured in the z-direction, varies. In the operating mode that is shown as an example in FIG. 5, four rows of 1 mm width are active, and, at both sides of these, respectively a row of 2 mm width is active.

In this case, the X-ray shadow image reconstruction unit 15 reconstructs the X-ray shadow image by converting the data from the detector system 5 into data as would be obtained from equidistant rows of equal width by means of interpolation or weighting. By interpolation, a conversion can ensue with respect to eight rows of respectively 1 mm width or with respect to six rows of respectively 1.33 mm, for example. By weighting, a conversion can ensue with respect to six rows of respectively 1 mm width, for example.

Therefore, corresponding to the absolute width of the detector rows, the data are utilized from the projection direction of the X-ray shadow image and, when the X-ray shadow image is reconstructed from measurement data in parallel geometry, the data from adjacent projection directions are utilized.

When the achievable image quality is reduced in the above described sense by means of the width of individual detector rows, or all detector rows, the resolution of the X-ray shadow image can be increased in the z-direction by utilizing the data that are offset by 180° and the re-interpolation of the fan data of the appertaining detector rows.

If diagnostically desired, a number of X-ray shadow images can be simultaneously generated in the described way, for example, for two projection directions that are offset to one another by 90°.

In the described exemplary embodiments, the relative movement between the measuring unit 1 and the support device 9 is generated by displacing the support device 9. However, in the framework of the invention, it is also possible to keep the support device 9 stationary and to displace the measuring unit 1 instead. It is also possible, in the framework of the invention, to effect the required relative movement by not only displacing the measuring unit 1 but also the support device 9.

The described exemplary embodiments employ CT devices of the $3^{rd}$ generation, i.e. the X-ray source and the detector system are displaced together around the system axis during the image generation. However, the invention can also be used in CT devices of the fourth generation, wherein only the X-ray source is displaced around the system axis and cooperates with a fixed detector ring, which has a planar array of detector elements.

The inventive method can also be employed with CT devices of the fifth generation, wherein the X-rays are emitted from a number of foci of one or more X-ray sources that are displaced around the system axis, with the detector system being a planar array of detector elements.

The CT devices utilized in the described exemplary embodiments employ a detector system with detector elements that are arranged in an orthogonal matrix. However, the invention can also be employed in CT devices, having a detector system with detector elements arranged in a different, planar array.

The described exemplary embodiments relate to the medical application of the inventive method, the invention can also be used outside of medicine, for example, baggage inspection or material testing.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a computed tomography apparatus, said computed tomography apparatus having a system axis and an X-ray source with a focus from which an X-ray beam is emitted, at least said focus being rotatable around said system axis, a detector system, on which said X-ray beam is incident, composed of a planar array of detector elements disposed in a plurality of rows proceeding substantially transversely to a direction of said system axis, and also arranged in columns, a support device for an examination subject disposed between said focus and said detector system, said method comprising the steps of:
   conducting a volume scanning of an examination subject on said support device by rotating at least said focus of said X-ray source around said system axis to produce data from said detector system from a plurality of projection directions;
   extracting data obtained from a selected projection direction for a plurality of said rows of said detector system obtained during said volume scanning; and
   reconstructing an X-ray shadow image from said extracted data.

2. A method as claimed in claim 1 comprising conducting said volume scanning as a spiral scan by producing a relative displacement, in a direction substantially parallel to said system axis, between said focus of said X-ray source and said detector system, and said support device, while rotating said focus of said X-ray source around said system axis.

3. A method as claimed in claim 1 comprising maintaining said support device, and said detector system and said focus of said X-ray source, in a fixed position relative to each other, relative to said system axis, during said volume scanning.

4. A method as claimed in claim 1 comprising reconstructing at least one tomogram from data acquired during said volume scanning, and extracting said data for producing said X-ray shadow image prior to reconstructing said at least one tomogram.

5. A method as claimed in claim 4 comprising combining data from a plurality of said rows of said detector system for reconstructing said tomogram, and combining said data subsequent to extracting said data for said X-ray shadow image.

6. A method as claimed in claim 1 comprising acquiring said data in said volume scan in fan geometry as fan geometry data, converting said fan geometry data into parallel geometry data, and extracting said data for reconstructing said x-ray shadow image after conversion into parallel geometry data.

7. A method as claimed in claim 1 comprising additionally extracting data for a projection direction that is offset by 180° relative to said selected projection direction, as further extracted data, and reconstructing said X-ray shadow image using said extracted data and said further extracted data.

8. A method as claimed in claim 1 wherein said detector system comprises a plurality of rows of detector elements of different widths and wherein, if said extracted data is from any of said rows with detector elements of different widths, converting said extracted data into data as would be acquired from a detector system with equidistant rows of detector elements of equal width.

* * * * *